United States Patent
Keller

(10) Patent No.: US 6,488,714 B2
(45) Date of Patent: Dec. 3, 2002

(54) PROSTHESIS SYSTEM

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/725,474

(22) Filed: Nov. 30, 2000

(65) Prior Publication Data

US 2001/0027346 A1 Oct. 4, 2001

(30) Foreign Application Priority Data

Dec. 2, 1999 (EP) .............................. 99124152

(51) Int. Cl.$^7$ .................................................. A61F 2/32
(52) U.S. Cl. ...................................... 623/22.12; 606/85
(58) Field of Search .................... 623/22.12; 606/84, 606/85, 86, 88, 89

(56) References Cited

U.S. PATENT DOCUMENTS

| 3,815,599 | A |   | 6/1974 | Deyerle |
| 4,671,275 | A |   | 6/1987 | Deyerle |
| 5,089,004 | A |   | 2/1992 | Averill et al. |
| 5,755,811 | A | * | 5/1998 | Tanamal et al. ............... 623/23 |
| 6,120,508 | A | * | 9/2000 | Grunig et al. ................. 606/85 |
| 6,319,256 | B1| * |11/2001 | Spotorno et al. ............. 606/85 |

FOREIGN PATENT DOCUMENTS

| EP | 0 359 097 | 3/1990 |
| FR | 2 719 464 | 10/1994 |
| WO | 98/42279  | 10/1998 |

* cited by examiner

*Primary Examiner*—Bruce Snow
(74) *Attorney, Agent, or Firm*—Morrison & Foerster LLP

(57) ABSTRACT

A prosthesis system consisting of an endoprosthesis with a shank which is to be introduced into the medullary canal of a bone, and of a rasp (20) which is similar in shape to the shank and is used to prepare a cavity for receiving the shank. Along much of its length, the rasp has an untoothed profile part (25) which, instead of excavating the spongy bone substance, compacts the latter and thus ensures a secure fit of the prosthesis. In the area corresponding to the untoothed area of the rasp (20), the prosthesis shank preferably has a rib which cuts like a wedge into the compacted spongy substance.

6 Claims, 1 Drawing Sheet

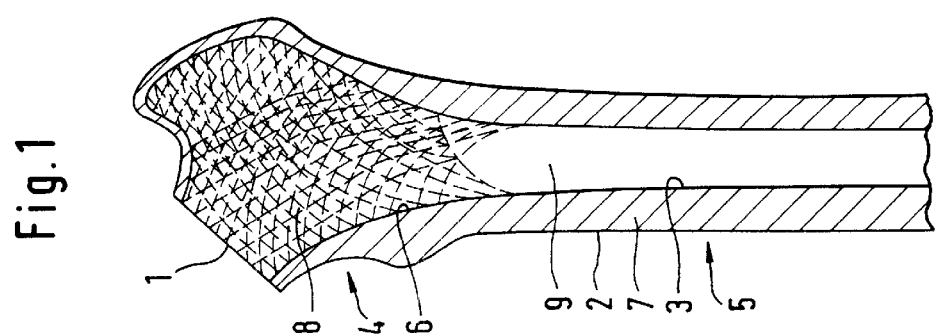
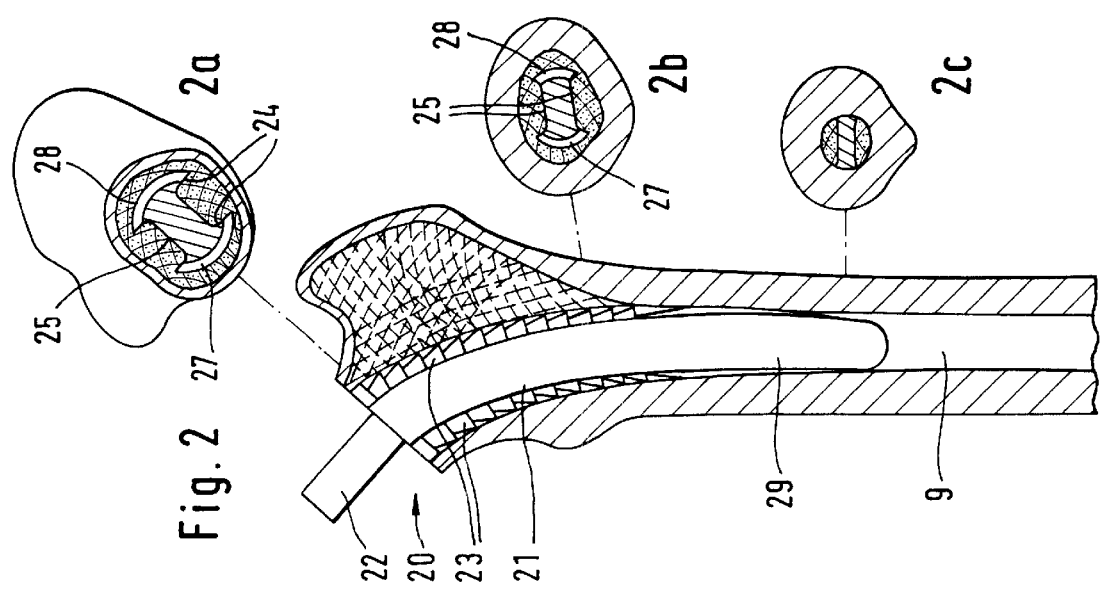
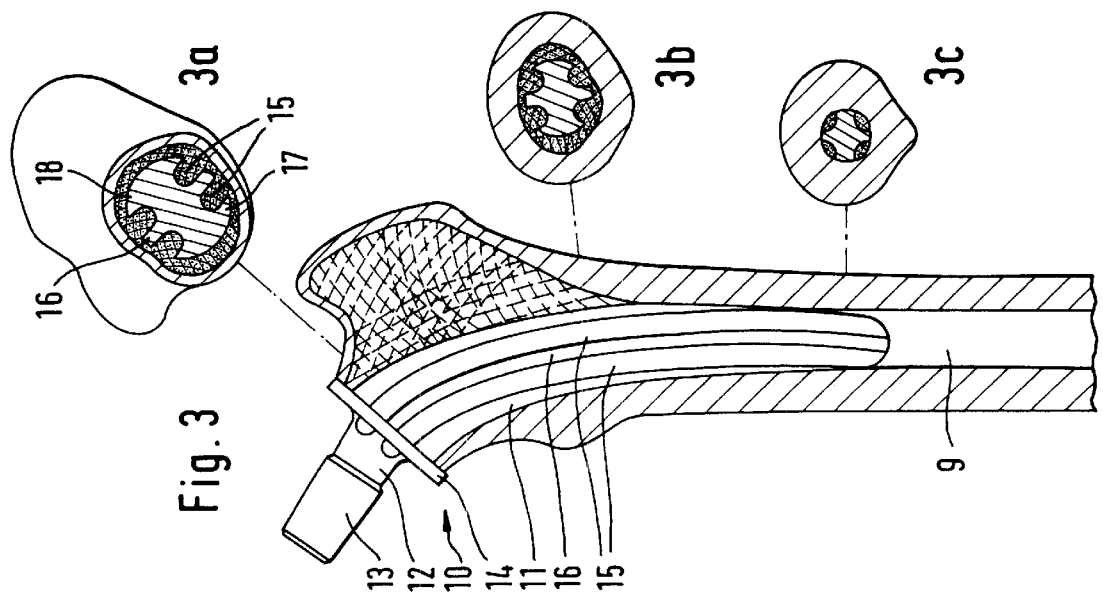

PROSTHESIS SYSTEM

BACKGROUND AND SUMMARY OF THE INVENTION

Endoprostheses are generally connected to the ends of long bones by anchoring a shank of the prosthesis in the cavity of the long bone. If this is to be done without using cement, then, in order to achieve sufficient anchoring stability, there must be substantial correspondence in shape between the prosthesis shank and the bone cavity intended to receive it. For this purpose, a rasp is used whose configuration corresponds with that of the prosthesis shank. After the epiphysis of the bone has been opened, and, if appropriate, after drilling through the epiphyseal spongy substance into the medullary canal of the diaphysis, the rasp is pushed into the bone to the position which the prosthesis shank is intended subsequently to assume. In doing so, the spongy bone is loosened by the rasp action of the instrument and for the most part removed from the bone.

U.S. Pat. No. 4,671,275 discloses a rasp which has an approximately rectangular cross section and is toothed only at the corners. Between these there are smooth, concave surfaces which do not exert any cutting or tearing action, but merely displace the bone material with which they make contact. This avoids the need to pack bone material around the prosthesis shank. The object of the invention is to make available a prosthesis system which consists of prosthesis and rasp and which permits an especially secure fit of the prosthesis shank in the bone. This is achieved by the features of claim 1 and preferably those of the dependent claims.

The invention is based on the observation that the increased strength of that area of the bone cavity generated by the untoothed profile part of the rasp improves the security of the prosthesis fit all the more the closer this area cooperates with the surface of the prosthesis shank. According to the invention, the shank therefore has at least one longitudinal rib arranged in that part of the prosthesis shank corresponding to the untoothed profile part of the rasp. Although it is advantageous for this rib to extend along the entire length of the shank, this is not absolutely essential, as long as a large part of the shank length is involved, preferably greater than one third, particularly preferably greater than two thirds, of the shank length.

The invention recognizes that a particularly secure prosthesis fit is obtained if the abovementioned longitudinal rib of the shank is absent in the profile of the rasp, at least over much of the length of the latter. In this case, the bone cavity created by the rasp in order to receive the shank has no groove at the location where the rib of the shank is situated. Instead, this groove is created only by the shank rib itself. As the shank is being introduced, it cuts like a wedge into the bone material. In this way, a bed is created in the bone cavity for receiving the prosthesis shank, in which bed the prosthesis shank, by virtue of its cross sectional shape, compresses the spongy substance at least in some areas and achieves optimum bone contact, preferably over greater than 70%, more preferably over greater than 80% of the shank surface.

The effect achieved according to the invention is further increased if the untoothed profile part of the rasp is dimensioned smaller than the corresponding part of the shank, with the result that, after implantation of the prosthesis shank, the surface of the bone cavity surrounds the latter with pre-stressing.

The invention is of particular importance for anchoring of a hip prosthesis which is to be implanted without cement. If the shank of the hip prosthesis is curved in approximation to Shenton's line, the untoothed profile part should be arranged on the ventral and/or dorsal aspect of the rasp, preferably on both aspects, while the rasp is toothed at least on the medial aspect. In this way, the surface of the bone cavity can be adapted very precisely to the surface shape of the shank in the medial area. First, this is important because the bone surface is fairly irregular there. Second, a relatively close approximation of the shank surface to the hard cortical bone is desired here. Thus, the remaining spongy layer, where the cortical bone has not been reached directly, is already comparatively compact and gives little play for compaction of the spongy bone substance, so that, in areas where pressure is too great, there is a risk of the cortical bone bursting if one were to rely solely on displacement of the spongy substance. For this reason, the toothing on the medial aspect of the rasp should be provided at least in the proximal area thereof. That means a section of about 4 to 7 cm in length on the medial aspect of the shank, measured from the upper end of the shank. The lateral aspect of the rasp is also expediently toothed, at least in the proximal section thereof.

By contrast, it is expedient if the distal section of the rasp is designed without sharp transverse edges on the medial and lateral aspects. This is because it is intended to fulfil a guide function, upon insertion of the rasp into the bone, by means of sliding along the inner surface of the cortical bone, primarily in the diaphyseal area, the aim of this being to avoid unnecessary damage to said cortical bone.

The untoothed areas on the ventral and/or dorsal aspects of the rasp preferably extend along the entire length of the rasp. Both aspects can be provided with the abovementioned longitudinal rib, which likewise is preferably arranged running along essentially the entire length of the shank. It is particularly advantageous if this rib is formed by a pair of grooves enclosing it on both sides, by which means a large contact surface is created for the intimate contact between the prosthesis shank and the compacted bone material. If this rib is absent in the rasp profile, only the groove cross sections are formed thereon, their bottom surfaces being connected essentially directly to each other. This creates, on the ventral and dorsal aspects of the rasp, extensive surfaces which are expediently spaced apart from each other by a distance which increases in a wedge shape from the direction of the distal end, in order to gradually compact the bone material along which the rasp slides as it is being pushed into the bone.

The concept of the invention can be summarized by stating that a prosthesis system consisting of prosthesis and rasp is made available which, in order to create the cavity for receiving the prosthesis, does not require prior excavation of bone material, but instead leaves the bone material in situ, and with which, by means of marked differences in shape between rasp and prosthesis shank, the spongy bone substance is compressed, upon insertion of the prosthesis shank, in such a way that an exercise-stable and secure fit of the prosthesis is achieved with high vital form closure to the bone.

BRIEF DESCRIPTION OF THE DRAWINGS

The invention is explained in greater detail below with reference to the drawing which depicts an advantageous illustrative embodiment and in which:

FIG. 1 shows a section in the lateral/medial plane of the proximal part of a femur;

FIG. 2 shows the sectional view according to FIG. 1 after a rasp has been introduced;

FIGS. 2a through 2c show cross sections through the arrangement according to FIG. 2, in the sectional planes indicated by dot-and-dash lines;

FIG. 3 shows the sectional view according to FIG. 1, after a prosthesis has been fitted, and FIGS. 3a through 3c show cross sectional views through the arrangement according to FIG. 3, in the sectional planes indicated by dot-and-dash lines.

DETAILED DESCRIPTION OF THE INVENTION

The proximal end of a femur is shown in FIG. 1 after the head of the joint has been resected along resection plane 1. The bone is formed on the outside by the hard cortical bone 7 which, in the drawing, lies between the outer surface 2 of the bone and the inner boundary line 3. The cortical bone is much thinner in the epiphyseal area 4 than in the diaphyseal area 5. This also applies (different than the diagrammatic representation in the drawing) in the area of Shenton's line 6, which is shown in the drawing as a monotonous arc line but which in reality presents irregularities. The line 6 in the drawing therefore represents an approximation to the cortical bone.

In the epiphyseal area 4 of the bone, the interior of the latter is filled by spongy bone substance 8, which is essentially absent in the medullary canal 9 of the diaphyseal area 5. Both contain soft marrow. The density of the spongy bone substance increases toward the cortical bone 7. The term medullary canal, as it is used in claim 1, is not limited to the cavity of the diaphysis, but also includes for the sake of simplicity the epiphyseal area into which the prosthesis is to be introduced.

In all of the drawings, the bone has been shown with its ventral (frontal) aspect toward the observer, said drawings representing the left femur and the left prosthesis. The dorsal aspect is facing in the other direction. The medial aspect is toward the left in the drawing, and the lateral aspect toward the right.

The endoprosthesis 10 consists of a shank 11, a neck 12 and a coupling piece 13 for connection to a joint head. The latter can also be connected in one piece to the neck. A neck bearing 14 can be provided lying on the resection surface 1.

The shank 11 is curved in an arc shape between a distal direction, which is approximately that of the diaphysis 5, and a proximal direction, which is similar to the direction of the natural neck of the joint. The curvature is essentially regular, so that the shank can be inserted into a correspondingly curved canal of the same shape which has been formed beforehand in the epiphyseal area of the bone. Slight deviations from the circular arc shape can be tolerated, especially in view of the fact that the thickness of the shank decreases toward the distal end.

The shank profile has an oval contour which can be seen in the cross sectional representations 3a through 3c. On the anterior and posterior aspects of the shank, two grooves 15 have in each case been cut into the profile, which grooves 15 delimit a rib 16 between them.

The grooves 15 and the rib 16 extend along the entire length of the shank, the thickness of the rib 16 and the width of the grooves remaining approximately constant. The distance between the groove bottoms of grooves lying opposite each other on the dorsal and ventral aspects increases slightly from the distal end to the proximal end of the shank. Since the rib 16 is situated in the central area of the shank cross section, it protrudes considerably further out from the profile core than do the medial 17 and lateral 18 cross sectional areas of the shank. As a result of the tapering of the shank from its proximal end toward the distal end, these medial and lateral cross sectional areas 17, 18 gradually disappear toward the distal end. The rib 16 is therefore configured with a large surface area both in the medial direction and also in the lateral direction. In the proximal half of the prosthesis shank, the height of each rib 16 is greater in cross section than the distance of the bottom surfaces of the grooves 15, enclosing it, from the axis of symmetry. This preferably also applies in the distal area of the prosthesis shank, as is shown clearly in FIGS. 3b and 3c.

In the proximal half of the shank length, the contour of the medial cross sectional area 17 essentially follows an arc of a circle (FIG. 3), the radius of curvature of which is approximate to that of Shenton's line. It will be appreciated that several sizes of prostheses are made available, permitting optimum shape adaptation to each size group of bones. The medial proximal shank surface is intended to bear on Shenton's line of the cortical bone or the relatively compact spongy bone substance which lies to the inside of this and which delimits the bone cavity formed to receive the prosthesis shank.

To form this cavity, the rasp 20 indicated in FIG. 2 is provided, consisting of a shank 21 and of a neck 22. With the neck and, if appropriate, other elements not shown in the drawing, it can be connected to an instrument handle to permit manipulation.

The shank 21 of the rasp 20 has a shape similar to that of the prosthesis shank 11. Comparing FIGS. 2a and 3a, FIGS. 2b and 3b, and FIGS. 2c and 3c, it will be apparent that the medial and lateral sections 17, 18 of the prosthesis profile are true imitations of the profile sections 27, 28 of the rasp 20. However, this is expediently done with slightly reduced dimensioning. The lateral-medial transverse measurement of the rasp is 0.2 to 2 mm, preferably 0.5 to 1 mm, smaller than the corresponding measurement of the prosthesis shank.

The sections 27, 28 of the rasp profile are provided with a toothing 23 which, at least in the area of Shenton's line, ensures a sufficiently defined bearing surface of the prosthesis shank. The toothing 23 is limited to the proximal part of the rasp length, namely (measured on the medial aspect) to preferably at least 4 cm, preferably about 5 to 6 cm. The remaining distal section of the rasp, whose total length (measured in a straight line between the center points of the proximal and distal ends of the rasp shank) is preferably between 10 and 12 cm, is untoothed in order not to damage the wall of the diaphyseal medullary canal 9 any more than is necessary. In addition, this ensures that the tip of the rasp is guided on the wall of the diaphyseal medullary canal in order to guarantee the correct positioning of the bone cavity produced by the rasp in the epiphyseal area.

The flanks of the grooves 15 of the prosthesis shank, adjoining the profile sections 17, 18, are also imitated at 24 in the rasp. However, the rib 16 is absent. In other words, the bottom surfaces of the grooves 15 in the case of the rasp are connected to each other in a straight line in order to form a continuous bottom surface 25. The distance between the bottom surfaces 25 lying opposite each other on the ventral and dorsal aspects of the rasp is approximately equal to the corresponding distance of the bottom surfaces of the grooves 15, but slightly smaller, namely by 0.2 to 2 mm, preferably 0.5 to 1 mm. The surfaces 25 and flanks 24 are untoothed, but the teeth of the profile sections 27, 28 run out into the flanks 24.

The mutual spacing of the bottom surfaces 25 is between 2 and 8 mm at the distal end and increases toward the proximal end by 3 to 7 mm. The bottom surfaces 25 are therefore of wedge-shaped design.

To prepare the bone cavity for receiving the prosthesis shank, first, starting from that point of the resection surface 1 of the bone at which the center point of the neck 12 is intended to lie, an opening is made through to the diaphyseal medullary canal 9 by means of a probe which does not excavate the substance but displaces it. The rasp 20 is then pushed into this opening, widening the epiphyseal spongy substance. In the last part of this movement, the teeth 23 form sufficiently precise bearing surfaces for the medial and lateral surfaces of the prosthesis shank 10. At the same time, the spongy bone substance contacted by the untoothed surfaces 24, 25 of the rasp is displaced and compacted. When the prosthesis shank is then pushed into the cavity, it finds its medial and lateral positioning surfaces which, because of the smaller dimensioning of the rasp, permit a secure fit. On the ventral and dorsal aspects, the rib 16 cuts like a wedge into the spongy substance located there and compacted by the rasp. This spongy substance is thereby further compacted. Further compaction is also achieved by the fact that the groove bottom 25 of the rasp is dimensioned smaller than the corresponding grooves 15. The large surface-area rib 16 thus sits securely in the compacted bone material.

The prosthesis shank thus acquires excellent initial stability in the bone. This guarantees a post-operative exercise-stable fit of the prosthesis in the loading direction medially and also against rotational forces. This additionally favors a vital connection of the prosthesis surface with the bone.

In this connection, a particular advantage is that the compressing of the spongy bone substance is made possible without at the same time creating any risk of the cortical bone bursting. This is based first on the fact that in those cross sectional areas where strong compaction would also lead to high radial stressing of the cortical bone, namely in the medial direction, the rasp is toothed, so that in these areas the rasp does not exert any compression effect. The compression which arises from the underdimensioning of the rasp compared with the prosthesis shank can be limited in a precise manner. Second, the cortical bone in the ventral and dorsal areas is relieved of the compression forces by virtue of the fact that the wedge-shaped untoothed surfaces 25 of the rasp are enclosed by the groove flanks 24 and therefore some of the compression force is taken up by these. This also applies upon insertion of the prosthesis shank into the bone cavity created in advance by the rasp. The compression surface which the rib 16 directs outward toward the cortical bone is relatively narrow (namely preferably narrower than 4 mm), and its compression action takes place principally in the area of the grooves 15, without thereby causing substantial loading of the cortical bone.

What is claimed is:

1. A prosthesis system, comprising:
   (a) an endoprosthesis configured as a hip prosthesis with a shank configured to be introduced into a medullary canal of a femoral bone and curved in approximation to Shenton's line and
   (b) a separate rasp corresponding to the shank which is similar in shape to the shank and is configured to be used to prepare a cavity in the bone for receiving the shank, said rasp having, along a substantial portion of its dorsal or medial aspect, an untoothed profile part dimensioned smaller than the corresponding part of the shank,
   the shank having at least one longitudinal rib formed on a part of the shank which corresponds to the untoothed profile part of the rasp, and, in the untoothed profile part of the rasp, there is no rib corresponding to the rib on the shank,
   wherein the toothing is limited to a proximal section of the rasp.

2. The prosthesis system as claimed in claim 1, wherein the shank, on its ventral or dorsal aspect, or both, has at least one longitudinal rib which is absent in the profile of the rasp.

3. The prosthesis system as claimed in claim 2, wherein the longitudinal rib runs along essentially the entire length of the shank.

4. The prosthesis system as claimed in claim 2 or 3, wherein the rib is formed by grooves enclosing it, and, in the profile of the rasp, the bottom surfaces of both grooves are connected essentially directly to each other.

5. The prosthesis system as claimed in claim 1, wherein two opposite untoothed surfaces of the rasp are spaced apart by a distance which increases in a wedge shape from the direction of the distal end.

6. A prosthesis system, comprising:
   (a) an endoprosthesis configured as a hip prosthesis with a shank configured to be introduced into a medullary canal of a femoral bone and curved in approximation to Shenton's line and
   (b) a separate rasp corresponding to the shank which is similar in shape to the shank and is configured to be used to prepare a cavity in the bone for receiving the shank, said rasp having, along a substantial portion of its dorsal or medial aspect, an untoothed profile part dimensioned smaller than the corresponding part of the shank,
   the shank having at least one longitudinal rib formed on a part of the shank which corresponds to the untoothed profile part of the rasp, and, in the untoothed profile part of the rasp, there is no rib corresponding to the rib on the shank,
   wherein the dorsal and ventral aspects of the rasp are untoothed along their entire lengths.

* * * * *